United States Patent [19]
Haffner et al.

[11] Patent Number: 6,096,014
[45] Date of Patent: *Aug. 1, 2000

[54] STABLE AND BREATHABLE FILMS OF IMPROVED TOUGHNESS AND METHOD OF MAKING THE SAME

[75] Inventors: William B. Haffner, Kennesaw; Ann L. McCormack, Cumming, both of Ga.; Vasily A. Topolkaraev, Appleton, Wis.

[73] Assignee: Kimberly-Clark Worldwide, Inc., Neenah, Wis.

[ * ] Notice: This patent issued on a continued prosecution application filed under 37 CFR 1.53(d), and is subject to the twenty year patent term provisions of 35 U.S.C. 154(a)(2).

[21] Appl. No.: 08/853,025

[22] Filed: May 8, 1997

Related U.S. Application Data

[63] Continuation of application No. 08/773,826, Dec. 27, 1996, abandoned.

[51] Int. Cl.$^7$ .............................. C08J 5/18; A61F 13/15; B29C 55/04
[52] U.S. Cl. ................................ 604/367; 521/92; 264/41
[58] Field of Search .............................. 604/367; 521/92; 264/41

[56] References Cited

U.S. PATENT DOCUMENTS

| | | |
|---|---|---|
| 4,552,709 | 11/1985 | Koger, II et al. . |
| 4,705,812 | 11/1987 | Ito et al. ................................... 521/92 |
| 4,793,956 | 12/1988 | Nogiwa et al. ............................ 264/41 |
| 4,868,222 | 9/1989 | Chau et al. . |
| 4,879,078 | 11/1989 | Antoon, Jr. ................................ 264/41 |
| 4,923,703 | 5/1990 | Antoon, Jr. . |
| 4,952,451 | 8/1990 | Mueller . |
| 5,110,677 | 5/1992 | Bamore et al. . |
| 5,140,073 | 8/1992 | Rolando et al. . |
| 5,209,984 | 5/1993 | Rolando et al. . |
| 5,258,419 | 11/1993 | Rolando et al. . |
| 5,264,219 | 11/1993 | Godbey et al. . |
| 5,296,291 | 3/1994 | Mueller . |
| 5,372,819 | 12/1994 | Godbey et al. . |
| 5,385,972 | 1/1995 | Yamamoto et al. ..................... 524/579 |
| 5,470,424 | 11/1995 | Isaac et al. .............................. 156/253 |
| 5,494,680 | 2/1996 | Peterson . |
| 5,509,142 | 4/1996 | Connell et al. ................................ 2/79 |
| 5,522,810 | 6/1996 | Allen, Jr. et al. ........................ 604/366 |

FOREIGN PATENT DOCUMENTS

| | | |
|---|---|---|
| 0 311 423 | 4/1989 | European Pat. Off. . |
| 0 659 808 A1 | 6/1995 | European Pat. Off. . |
| 0 779 325 A2 | 6/1997 | European Pat. Off. . |
| 0 779325 A2 | 6/1997 | European Pat. Off. . |
| WO 96/19346 | 6/1996 | WIPO . |

OTHER PUBLICATIONS

"Tough Metallocene LLDPE Enters the Big Time", *Canadian Plastics*, p. 19, Apr., 1996, from DIALOG database (1996).
"LLDPE Resin Advances Promise New Growth in Tough Film", *Modern Plastics International*, p. 38, Jun., 1995, from DIALOG database (1996).
"LLDPE Resin Advances Promise New Growth in Tough Film", *Modern Plastics*, v72, n6, p42(4), Jun., 1995, from DIALOG database (1996).
"Navigating the Materials Malestrom", *Modern Plastics*, p. 47, vol. 72, No. 5, May, 1995, from DIALOG database (1996).
Leaversuch, R.D., "Supertough PE Films Aid Downgauging Drive", *Modern Plastics Int.*, 24, No. 8, pp. 55/9, Aug., 1994, from DIALOG database (1996).
Leaversuch, R.D., "Supertough PE Films Aid Downgaging of Packaging", *Modern Plastics*, p. 19, vol. 71, No. 8, Aug., 1994, from DIALOG database (1996).
"New Generation Dowlex Family of Resins Debuts From Dow Plastics", *Food Engineering*, V64, n12, p50(2), Dec., 1992, from DIALOG database (1996).
"Kangaroo Brands Jumps At an Opportunity", *Packag. Dig.*, vol. 30, No. 4, pp. 42, 44, 46, Apr., 1993, from DIALOG database (1996).
"Polyethylene—Linear Low Density; Film", *Mod. Plast. Int.*, 22, No. 10, p. 151, Oct., 1992, from DIALOG database (1996).
"Dow Says Octene LLDPEs Improve Blown and Cast Film Properties", *Modern Plastics*, p. 135, Oct., 1992, from DIALOG database (1996).
"High–Performance PEs for Packaging", *Plastics Technology*, v38, n11, p21(3), Oct., 1992, from DIALOG database (1996).

*Primary Examiner*—John G. Weiss
*Assistant Examiner*—Miley Craig Peppers, III

[57] ABSTRACT

Uniaxially oriented microporous breathable films having exceptional toughness transverse to the direction of orientation are disclosed herein. Such films include a particulate filler and a nonelastic material including a copolymer of ethylene with at least one $C_4$–$C_8$ α-olefin monomer, such copolymers being described in the trade as "super tough", "next generation", etc., and being prepared with "new" or "improved" catalyst systems or with metallocene or similar single-site catalysts. A method of manufacture is also disclosed.

36 Claims, 2 Drawing Sheets

STABLE AND BREATHABLE FILMS OF IMPROVED TOUGHNESS AND METHOD OF MAKING THE SAME

CROSS-REFERENCE TO RELATED APPLICATIONS

This application is a continuation of U.S. application Ser. No. 08/773,826, filed Dec. 27, 1996, now abandoned.

FIELD OF INVENTION

The present invention is directed to breathable thermoplastic films utilizing copolymers of ethylene and at least one $C_4$–$C_8$ α-olefin. In addition, the present invention is directed to a method of making such films.

BACKGROUND OF THE INVENTION

The present invention is directed to breathable thermoplastic films. Such materials have a wide variety of uses, especially in the areas of limited use and disposable items.

Films have been traditionally used to provide barrier properties in limited use or disposable items. By limited use or disposable, it is meant that the product and/or component is used only a small number of times or possibly only once before being discarded. Examples of such products include, but are not limited to, surgical and health care related products such as surgical drapes and gowns, disposable work wear such as coveralls and lab coats and personal care absorbent products such as diapers, training pants, incontinence garments, sanitary napkins, bandages, wipes and the like. In personal care absorbent products such as infant diapers and adult incontinence products, films are used as the outer covers with the purpose of preventing body wastes from contaminating the clothing, bedding and other aspects of the surrounding environment of use. In the area of protective apparel including hospital gowns, films are used to prevent cross exchange of microorganisms between the wearer and the patient.

While these films can be effective barriers, they are not aesthetically pleasing because their surfaces are smooth and either feel slick or tacky. They are also visually flat and "plasticy" thereby making them less desirable in apparel applications and other uses where they are in contact with human skin. It would be more preferable if these items were more cloth-like from both a tactile and visual standpoint. For example, infant diapers that have the feel and appearance of traditional cloth undergarments are perceived as premium products and may, in some cases, overcome the tendency to believe that they need to be covered by outer garments for aesthetic reasons. Garment-like adult incontinence products could improve the self-image of the incontinent individual. In addition, more garment-like isolation gowns would help the hospital environment feel less foreign and threatening to the patient and increase the comfort of the wearer. It is also preferable to have films that can make an outercover material with more elastic give and recovery to provide better fit and comfort.

Lamination of films has been used to create materials which are both liquid-impervious and somewhat cloth-like in appearance and texture. The outer covers on disposable diapers are but one example as can be seen in coassigned U.S. Pat. No. 4,818,600 dated Apr. 4, 1989 and U.S. Pat. No. 4,725,473 dated Feb. 16, 1988. Surgical gowns and drapes are other examples. See, in this regard, coassigned U.S. Pat. No. 4,379,102 dated Apr. 5, 1983.

A primary purpose of the film in such laminations is to provide barrier properties. There is also a need for such laminates to be breathable so that they have the ability to transmit moisture vapor. Apparel made from laminates of these breathable or microporous films are more comfortable to wear by reducing the moisture vapor concentration and the consequent skin hydration underneath the apparel item. However, the pore size in breathable films cannot be too large, especially in protective apparel applications where chemical vapor penetration presents a contamination risk to the wearer.

The conventional process for obtaining a breathable microporous film has been to stretch a thermoplastic film containing filler. Microvoids are created by the filler particles during the stretching process. The film is usually heated prior to these drawing processes to make the film more plastic or malleable. This drawing or stretching also orients the molecular structure within the film which increases its strength and durability. The molecular orientation caused by stretching is desired to improve durability.

A film can be stretched in the machine-direction or the cross-machine direction. Stretching the film in the cross direction is particularly challenging because forces must be applied to the edges of the film to cause it to elongate width-wise. Tenter frames are commonly used. In contrast, stretching the film in the machine direction is relatively easy. It is only necessary to increase the draw, or speed ratio, between two rollers while the film is in the heated or plastic state. There is a durability problem, however, with uni-directionally-stretched films, be it machine direction or cross-direction. Uni-directional stretching causes molecular orientation only in the stretched direction. This results in films that are easily torn or split along that dimension. For example, a machine-directionally oriented film has a propensity to split or tear along the machine direction. Also, the tensile characteristics of the (machine-directionally stretched) film are dramatically increased in the machine direction, but the tensile strength in the cross-direction is significantly inferior to that of the machine direction. Thus, for example, if at the same time that the CD strength of the film decreases, the CD break elongation is also reduced, the film can split very easily in use, and an article made with it, such as a diaper, may leak, obviously an undesirable effect.

These durability problems with uni-directionally stretched or oriented films are well known. Two approaches are commonly used to obviate the product durability problems resulting from these highly isotropic strength characteristics. The first is to stretch-orient the film in both the machine and cross direction. Films that have been biaxially stretched have more balanced strength properties. The second approach is to combine into a laminate one layer of machine directionally oriented film with one layer of cross-directionally oriented film.

One other manufacturing issue is the strength of "aged" films. In commercial manufacturing operations, "fresh" films such as newly extruded films are generally not available for orientation. Extruded films are often set aside or stored for later orientation, usually at room temperature. During this storage period, a change in morphology of the polymer may occur, which change could be the cause of film property changes. Orientation of such aged film often results in products with lower durability characteristics such as lower CD Peak Strain (or cross directional break elongation), a critical property, for example, for the durability of a diaper outer cover made from this film.

There is therefore a need for an elastic breathable film and process that provides a film with both the cloth-like aesthetics and the durability and comfort that are desired.

SUMMARY OF THE INVENTION

The present invention relates to a breathable thermoplastic film that includes a linear low density polyethylene resin material including copolymers of ethylene and $C_4$-$C_8$ $\alpha$-olefin monomer and a filler present in an amount that is at least 40% by weight of the filled resin, wherein the filler has a particle size that contributes to pore formation. Preferably, the film includes from about 40 to about 65% filler by weight of the filled resin. In one application, where the minimum desired water vapor transmission rate is about 1,500 g/m²/24 hours, the amount of filler present is about 48 weight percent.

The present invention also is directed to a process for preparing a breathable film of the present invention, including providing a polymeric resin including a linear low density polyethylene resin material; adding to the resin at least 40% by weight of a filler having a particle size that contributes to pore formation to form a filled resin; forming a film having a first length from the filled resin; and stretching the film to form a microporous film. The process of the invention is applicable to films formed by various processes, i.e., cast or blown films. In one embodiment of the invention, the microporous film is stretched to a second length that is from about 160 to about 400% of the first length. In another embodiment, the film is annealed following stretching.

The preferred film of the present invention has a water vapor transmission rate of from about 300 to about 4,500 grams per square meter per 24 hours (measured by ASTM Standard Test E 96-80 with Celgard® 2500 as control).

Such films have a wide variety of uses including, but not limited to, applications in personal care absorbent articles including diapers, training pants, sanitary napkins, incontinence devices, bandages and the like. These same films also may be used in items such as surgical drapes and gowns as well as various articles of clothing either as the entire article or simply as a component thereof.

Having thus described the invention in detail, it should be appreciated that various modifications and changes can be made to the present invention without departing from the spirit and scope of the following claims.

DETAILED DESCRIPTION OF THE PREFERRED EMBODIMENT

Figure 1:
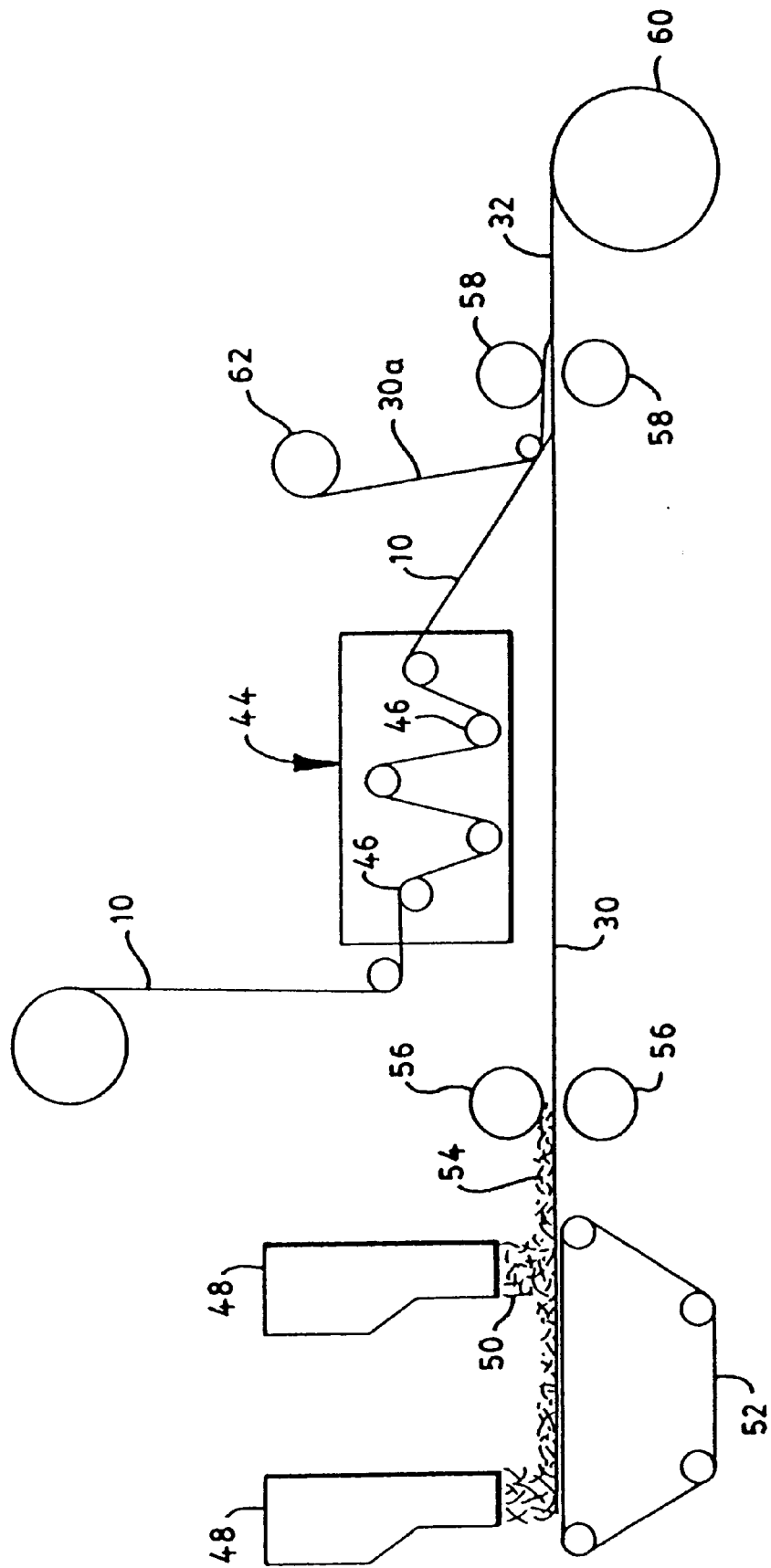
FIG. 1 is a schematic side view of a process for forming a film according to the present invention.

The present invention is directed to breathable thermoplastic films that include copolymers of ethylene and $C_4$-$C_8$ $\alpha$-olefin monomer.

One particularly useful example is known as "super-octene." The term "super-octene" as used herein includes those linear low density polyethylene (LLDPE) materials that are produced by the polymerization of ethylene and 1-octene comonomer and designated Dowlex® NG brand ("NG resin"), available from Dow Chemical Corporation of Midland, Mich. The "super-octene" resin are made with an improved catalyst system other than "metallocene" or Insite®. Suitable "super-octene" resins useful in the present invention include, for example, Dowlex® NG 3347A and Dowlex® NG 3310, both of which contain about 7% octene (nominal weight %), 93% ethylene. While not wishing to be bound by the following theory, it is postulated that the improved catalyst regulates the molecular weight/molecular weight distribution as well as comonomer placement and branching on the polymer molecule more precisely than conventional catalysts. It is possible, for example, that as a result of the improved technology, the NG resins have narrower molecular weight distribution, more homogeneous branching distribution as well as smaller highly branched low density and unbranched high density fractions. The physical characteristics of unfilled films made from super-octene resins do not distinguish this resin from conventional LLDPE resins, as illustrated in Table A below. Table A lists physical data of Dowlex® NG 3347A and, for comparison, data of certain "conventional" LLDPE resins, Dowlex® 2045 and 2244A.

TABLE A

|  | NG 3347A | Dowlex ® 2045 | Dowlex ® 2244A |
|---|---|---|---|
| Melt index, gm/10 min. (an indication of MW) | 2.3 | 1.0 | 3.3 |
| Density, gm/cc | 0.917 | 0.920 | 0.9155 |
| Film extrusion method | blown | blown | cast |
| (a) Tensile yield, MPa, | 9.0/8.3 | 10.3/11.0 | 7.6/6.9 |
| MD/CD |  |  |  |
| (b) Break tensile, MPa, MD/CD | 60/34 | 51.9/40.0 | 54.5/37.3 |
| (c) Break elongation, %, MD/CD | 550/750 | 600/750 | 580/780 |
| (d) Elmendorf tear, gm, MD/CD | 330/540 | 375/750 | 350/580 |

As can be seen from Table A above, the typical properties ((a) through (d)) of unfilled films from these various resins are not remarkably different. Minor variations could be explained by variations in melt index and $\alpha$-olefins density or crystallinity.

Other ethylene-based copolymers with $C_4$-$C_8$ $\alpha$-olefins are also useful in the present invention including, for example, materials commercially from Exxon Corporation under the brand name Exact™ These materials are all prepared with a "new" or "improved" catalyst system with respect to the metallocene or similar single-site catalysts.

Other suitable ethylene-based copolymers with $C_4$–$C_8$ $\alpha$-olefin monomers of the present invention include non-elastic metallocene-catalyzed polymers. The term "metallocene-catalyzed polymers" as used herein includes those polymer materials that are produced by the polymerization of at least ethylene using metallocenes or constrained geometry catalysts, a class of organometallic complexes, as catalysts. For example, a common metallocene is ferrocene, a complex with a metal sandwiched between two cyclopentadienyl (Cp) ligands. Metallocene process catalysts include bis(n-butylcyclopentadienyl)titanium dichloride, bis(n-butylcyclopentadienyl)zirconium dichloride, bis (cyclopentadienyl)scandium chloride, bis(indenyl) zirconium dichloride, bis(methylcyclopentadienyl)titanium dichloride, bis(methylcyclopentadienyl)zirconium dichloride, cobaltocene, cyclopentadienyltitanium trichloride, ferrocene, hafnocene dichloride, isopropyl (cyclopentadienyl,-1-flourenyl)zirconium dichloride, molybdocene dichloride, nickelocene, niobocene dichloride, ruthenocene, titanocene dichloride, zirconocene chloride hydride, zirconocene dichloride, among others. A more exhaustive list of such compounds is included in U.S. Pat. No. 5,374,696 to Rosen et al. and assigned to the Dow Chemical Company. Such compounds are also discussed in U.S. Pat. No. 5,064,802 to Stevens et al. and also assigned to Dow. The before-mentioned entire patents are incorporated herein by reference.

The metallocene process, and particularly the catalysts and catalyst support systems are the subject of a number of patents. U.S. Pat. No. 4,542,199 to Kaminsky et al. describes a procedure wherein MAO is added to toluene, the metallocene catalyst of the general formula (cyclopentadienyl) 2MeRHal wherein Me is a transition metal, Hal is a halogen and R is cyclopentadienyl or a C1 to C6 alkyl radical or a halogen, is added, and ethylene is then added to form polyethylene. U.S. Pat. No. 5,189,192 to LaPointe et al. and assigned to Dow Chemical describes a process for preparing addition polymerization catalysts via metal center oxidation. U.S. Pat. No. 5,352,749 to Exxon Chemical Patents, Inc. describes a method for polymerizing monomers in fluidized beds. U.S. Pat. No. 5,349,100 describes chiral metallocene compounds and preparation thereof by creation of a chiral center by enantioselective hydride transfer. Co-catalysts are materials such as methylaluminoxane (MAO) which is the most common, other alkylaluminums and boron containing compounds like tris- (pentafluorophenyl)boron, lithium tetrakis(pentafluorophenyl)boron, and dimethylanilinium tetrakis(pentafluorophenyl)boron. Research is continuing on other co-catalyst systems or the possibility of minimizing or even eliminating the alkylaluminums because of handling and product contamination issues. The important point is that the metallocene catalyst be activated or ionized to a cationic form for reaction with the monomer(s) to be polymerized.

The metallocene-catalyzed ethylene-based polymers used in the present invention impart stretch and recovery properties to the film. Preferably, the metallocene catalyzed ethylene-based polymer is selected from copolymers of ethylene and 1-butene, copolymers of ethylene and 1-hexene, copolymers of ethylene and 1-octene and combinations thereof. In particular, preferred materials include Affinity™ brand metallocene-derived copolymers of ethylene and 1-octene, both available from Dow Plastics of Freeport, Tex. Also preferred are Exact™ brand metallocene-derived copolymers of ethylene and 1-butene and copolymers of ethylene and 1-hexene, available from Exxon Chemical Company of Houston, Tex. In general, the metallocene-derived ethylene-based polymers of the present invention have a density of at least 0.900 g/cc.

At least one copolymer of ethylene and $C_4$-$C_8$ α-olefin monomer is the major polymeric component of the film of the present invention. Preferably, the film of the present invention contains at least 30 percent, more preferably about 40–50 percent by weight of the filled film composition. Other polymeric components may also be present so long as they do not adversely affect the desired characteristics of the film.

In addition to the polymeric material, the film layer also includes a filler which enables development of micropores during orientation of the film. As used herein a "filler" is meant to include particulates and other forms of materials which can be added to the polymer and which will not chemically interfere with or adversely affect the extruded film but is able to be uniformly dispersed throughout the film. Generally, the fillers will be in particulate form and usually will have somewhat of a spherical shape with average particle sizes in the range of about 0.5 to about 8 microns. In addition, the film will usually contain filler in an amount of at least 40 percent(%), preferably about 45 to about 65 percent, based upon the total weight of the film layer. More preferably, from about 45 to about 55 percent of filler is present in the film. Both organic and inorganic fillers are contemplated to be within the scope of the present invention provided that they do not interfere with the film formation process, the breathability of the resultant film or its ability to bond to another layer such as a fibrous polyolefin nonwoven web.

Examples of fillers include calcium carbonate ($CaCO_3$), various kinds of clay, silica ($SiO_2$), alumina, barium sulfate, sodium carbonate, talc, magnesium sulfate, titanium dioxide, zeolites, aluminum sulfate, cellulose-type powders, diatomaceous earth, magnesium sulfate, magnesium carbonate, barium carbonate, kaolin, mica, carbon, calcium oxide, magnesium oxide, aluminum hydroxide, pulp powder, wood powder, cellulose derivative, polymer. particles, chitin and chitin derivatives. The filler particles may optionally be coated with a fatty acid, such as stearic acid or behenic acid which may facilitate the free flow of the particles (in bulk) and their ease of dispersion into the polymer matrix.

Generally, it has been possible to produce films with a water vapor transmission rate (WVTR) of at least about 300 grams per square meter per 24 hours, measured by the ASTM E-96-80 WVTR test (using Celgard® 2500 as control). In general, factors that affect the amount of breathability include the amount of filler, the film stretching conditions (e.g., whether it is performed at ambient or elevated temperatures), orientation ratio, and film thickness. Generally, the WVTR of the film of the present invention that may be used as a component in a limited-use or disposable item is from about 300 to about 4,500, and, in one application, preferably at least about 1,500 $g/m^2/24$ hrs. In addition, the preferred films of the present invention, when stretched in the machine direction, have superior extensibility and increased resistance to failure around film flaws.

These properties can be obtained by first preparing a polymeric resin of a super-octene LLDPE resin, filling the resin with filler, extruding a film from the filled resin and thereafter stretching or orienting the filled film in at least one direction, usually, the machine direction. As explained in greater detail below, the resultant film is microporous and has increased strength properties in the orientation direction.

Processes for forming filled films and orienting them are well-known to those skilled in the art. In general, a process for forming oriented filled film 10 is shown in FIG. 1 of the drawings. Film 10 is unwound and directed to a film stretching unit 44 such as a machine direction orienter, which is a commercially available device from vendors such as the Marshall and Williams Company of Providence, R.I. Such an apparatus 44 has a plurality of stretching rollers 46 moving at progressively faster speeds relative to the pair disposed before them. These rollers 46 apply an amount of stress and thereby progressively stretched filled film 10 to a stretch length in the machine direction of the film which is the direction of travel of filled film 10 through the process as shown in FIG. 1. The stretch rollers 46 may be heated for better processing. Preferably, unit 44 also includes rollers (not shown) upstream and/or downstream from the stretch rollers 46 that can be used to preheat the film 10 before orienting and/or anneal (or cool) it after stretching. The purpose of the annealing is to stabilize the film so that it will shrink less or not at all when it is exposed to elevated temperatures during subsequent processing, storage, transportation, or product use.

Uniaxial orientation is a well known art in the plastics film industry. Films are often oriented to enhance their strength and other physical properties. The most common and simplest kind of uniaxial orientation is in the machine direction (MD) on equipment often called machine direction orientor, or MDO for short. Various MDO designs are used in the industry, all of which use temperature-controlled rollers for heating or cooling and transport of the film being processed. Stretching is accomplished between the slow nip and the fast nip, the slow nip holding the film back, and the fast nip accelerating the film causing it to become longer and at the same time thinner and somewhat narrower (necked). In practical terms the degree of orientation is usually described as the stretch ratio, such as 3x or 4x, which is the ratio of the surface speed of fast nip to the surface speed of the slow nip. The slow nip is generally preceded by preheat rolls which can heat the film to the desired stretching temperature, and the fast nip is followed by rolls to heat the film to some annealing temperature. Cooling roll(s) may be used to cool the stretched film before further processing.

Polymer films are oriented above the glass transition temperature and below the melting temperature of the polymers used. Good film properties can be obtained at relatively low stretch temperatures, such as room temperature. However, higher temperature may be used for ease of processing and to allow practical processing speeds. For example, the preheat and slow nip may be at 160° F., fast nip and first annealing roll may be varied from room temperature to about 215° F., and the last annealing roll may be at about 200, 210, or 215° F. Processing speeds may be at about 80–100 feet per minute (fpm) on the slow nip, and about 320–425 (fpm) on the fast nip.

The useful degree of stretching for breathable films is somewhat different for different polymers used. To avoid unstretched segments or spots in the film, that is, to make fully oriented ("whitened") film, the lowest stretch ratio is preferably about 3x. Good results may be obtained at about 4x–4.25x. If a film is "overstretched" (generally above about 5x), it could become excessively splitty. At the stretched length, a plurality of micropores form in the film 10. If desired, film 10 is directed out of apparatus 44 so that the stress is removed to allow the stretched film 10 to relax.

Figure 2:
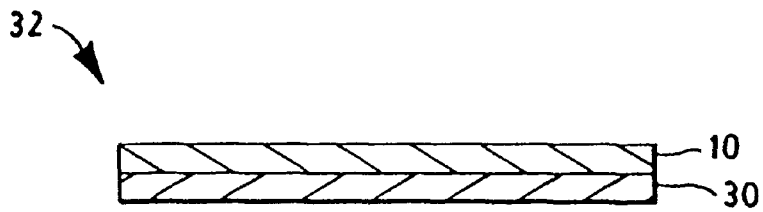
FIG. 2 is a cross-section side view of a film/nonwoven laminate according to the present invention.

Oftentimes it may be desirable to laminate filled film 10 to one or more substrates or support layers 20 such as is shown in FIG. 2. Lamination of film may enhance the strength and thus durability of the film. If desired, filled film 10 may be attached to one or more support layers 30 to form a laminate 32. Referring again to FIG. 1, a conventional fibrous nonwoven web-forming apparatus 48, such as a pair of spunbond machines, is used to form the support layer 30. The long, essentially continuous fibers 50 are deposited onto a forming wire 52 as an unbonded web 54 and the unbonded web 54 is then sent through a pair of bonding rolls 56 to bond the fibers together and increase the tear strength of the resultant web support layer 30. One or both of the rolls are often heated to aid in bonding. Typically, one of the rolls 56 is also patterned so as to impart a discrete bond pattern with a prescribed bond surface area to the web 30. The other roll is usually a smooth anvil roll but this roll also may be patterned if so desired. Once filled film 10 has been sufficiently stretched and the support layer 30 has been formed, the two layers are brought together and laminated to one another using a pair of laminating rolls or other means 58. As with the bonding rolls 56, the laminating rolls 58 may be heated. Also, at least one of the rolls may be patterned to create a discrete bond pattern with a prescribed bond surface area for the resultant laminate 32. Generally, the maximum bond point surface area for a given area of surface on one side of the laminate 32 will not exceed about 50 percent of the total surface area. There are a number of discrete bond patterns which may be used. See, for example, Brock et al., U.S. Pat. No. 4,041,203 which is incorporated herein by reference in its entirety. Once the laminate 32 exists the laminating rolls 58, it may be wound up into a roll 60 for subsequent processing. Alternatively, the laminate 32 may continue in-line for further processing or conversion.

While the support layers 30 and film 10 shown in FIG. 1 were bonded together through thermal point bonding, other bonding means can also be used. Suitable alternatives include, for example, adhesive bonding and the use of tackifiers. In adhesive bonding, an adhesive such as a hot melt adhesive is applied between the film and fiber to bind the film and fiber together. The adhesive can be applied by, for example, melt spraying, printing or meltblowing. Various types of adhesives are available, including those produced from amorphous polyalphaolefins, ethylene vinyl acetate-based hot melts, and Kraton® brand adhesives available from Shell Chemical of Houston, Tex. and Rextac™ Brand Adhesives from Rexene of Odessa, Tex.

When the film and support layer(s) is bonded with tackifiers, the tackifier may be incorporated into the film itself. The tackifier essentially serves to increase adhesion between the film and fiber layers. The film and fiber laminate may subsequently be thermally point-bonded, although generally very little heat is required since the tackifier tends to increase the pressure sensitivity of the film and a bond somewhat like and adhesive bond can be formed. Examples of useful tackifiers include Wingtack™ 95, available from Goodyear Tire & Rubber Co. of Akron, Ohio, and Escorez™ 5300, available from Exxon Chemical Company of Houston, Tex.

The support layers 30 as shown in FIG. 2 are fibrous nonwoven webs. The manufacture of such fibrous nonwoven webs is known. Such fibrous nonwoven webs can add additional properties to filled film 10, such as a more soft, cloth-like feel. This is particularly advantageous when filled film 10 is being used as a barrier layer to liquids in such applications as outer covers for personal care absorbent articles and as barrier materials for hospital, surgical, and clean room applications such as, for example, surgical drapes, gowns and other forms of apparel. Attachment of the support layers 30 to the filled film 10 may be by the use of a separate adhesive such as hot-melt and solvent based adhesives or through the use of heat and/or pressure (also known as thermal bonding) as with heated bonding rolls.

The support layer in a laminate containing the film layer of the present invention can be necked polypropylene spunbond, crimped polypropylene spunbond, bonded carded webs, elastomeric spunbond or meltblown fabrics produced from elastomeric resins. A particularly advantageous support layer is a fibrous nonwoven web. Such webs may be formed from a number of processes including, but not limited to, spunbonding, meltblowing and bonded carded web processes. Meltblown fibers are formed by extruding molten thermoplastic material through a plurality of fine, usually circular, capillaries as molten threads or filaments into a high velocity usually heated gas stream such as air, which attenuates the filaments of molten thermoplastic material to reduce their diameters. Thereafter, the meltblown fibers are carried by the high velocity usually heated gas stream and are deposited on a collecting surface to form a web of randomly dispersed meltblown fibers. The meltblown process is well-known and is described in various patents and publications, including NRL Report 4364, "Manufacture of Super-Fine Organic Fibers" by B. A. Wendt, E. L. Boone and D. D. Fluharty; NRL Report 5265, "An Improved Device For The Formation of Super-Fine Thermoplastic Fibers" by K. D. Lawrence, R. T. Lukas, J. A. Young; U.S. Pat. No. 3,676,242, issued Jul. 11, 1972, to Prentice; and U.S. Pat. No. 3,849,241, issued Nov. 19, 1974, to Buntin, et al. The foregoing references are incorporated herein by reference in their entirety.

Spunbond fibers are formed by extruding a molten thermoplastic material as filaments from a plurality of fine, usually circular, capillaries in a spinnerette with the diameter of the extruded filaments then being rapidly reduced, for example, by non-educative or educative fluid-drawing or other well-known spunbonding mechanisms. The production of spunbond nonwoven webs is illustrated in patents such as Appel et al., U.S. Pat. No. 4,340,563; Matsuki, et al., U.S. Pat. No. 3,802,817; Dorschner et al., U.S. Pat. No. 3,692,618; Kinney, U.S. Pat. Nos. 3,338,992 and 3,341,394; Levy, U.S. Pat. No. 3,276,944; Peterson, U.S. Pat. No. 3,502,538; Hartman, U.S. Pat. No. 3,502,763; Dobo et al., U.S. Pat. No. 3,542,615; and Harmon, Canadian Patent No. 803,714. All of the foregoing references are incorporated herein by reference in their entirety.

A plurality of support layers 30 also may be used. Examples of such materials can include, for example, spunbond/meltblown laminates and spunbond/meltblown/spunbond laminates such as are taught in Brock et al., U.S. Pat. No. 4,041,203 which is incorporated herein by reference in its entirety.

Bonded carded webs are made from staple fibers which are usually purchased in bales. The bales are placed in a picker which separates the fibers. Next the fibers are sent through a combing or carding unit which further breaks apart and aligns the staple fibers in the machine direction so as to form a machine direction-oriented fibrous nonwoven web. Once the web has been formed, it is then bonded by one or more of several bonding methods. One bonding method is powder bonding wherein a powdered adhesive is distributed throughout the web and then activated, usually by heating the web and adhesive with hot air. Another bonding method is pattern bonding wherein heated calender rolls or ultrasonic bonding equipment is used to bond the fibers together, usually in a localized bond pattern though the web can be bonded across its entire surface if so desired. When using bicomponent staple fibers, through-air bonding equipment is, for many applications, especially advantageous.

The process shown in FIG. 1 also may be used to create a three layer laminate. The only modification to the previously described process is to feed a supply 62 of a second fibrous nonwoven web support layer 30a into the laminating rolls 58 on a side of filled film 10 opposite that of the other fibrous nonwoven web support layer 30. As shown in FIG. 1, one or both of the support layers may be formed directly in-line, as is support layer 30. Alternatively, the supply of one or both support layers may be in the form of a preformed roll 62, as is support layer 30a. In either event, the second support layer 30a is fed into the laminating rolls 58 and is laminated to filled film 10 in the same fashion as the first support layer 30.

Figure 3:
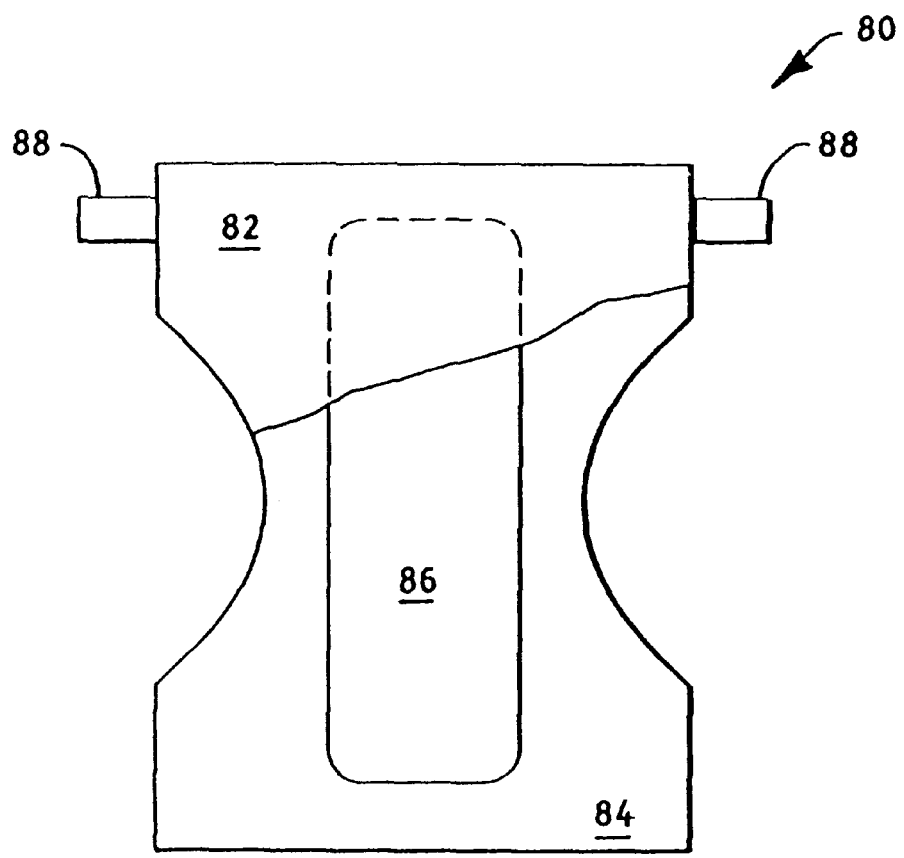
FIG. 3 is a partially cut away top plan view of an exemplary personal care absorbent article, in this case a diaper, which may utilize a film made according to the present invention.

As has been stated previously, filled film 10 and the breathable laminate 32 may be used in a wide variety of applications not the least of which includes personal care absorbent articles such as diapers, training pants, incontinence devices and feminine hygiene products such as sanitary napkins. An exemplary article 80, in this case a diaper, is shown in FIG. 3 of the drawings. Referring to FIG. 3, most such personal care absorbent articles 80 include a liquid permeable top sheet or liner 82, a back sheet or outercover 84 and an absorbent core 86 disposed between and contained by the top sheet 82 and back sheet 84. Articles 80 such as diapers may also include some type of fastening means 88 such as adhesive fastening tapes or mechanical hook and loop type fasteners to maintain the garment in place on the wearer. The fastening system may contain stretch material to form "stretch ears" for greater comfort.

Filled film 10 by itself or in other forms such as the film/support layer laminate 32 may be used to form various portions of the article including, but not limited to, stretched ears, the top and the back sheet 84. If the film or laminate is to be used as the liner 82, it will have to be apertured or otherwise made to be liquid permeable. When using a film/nonwoven laminate as the outercover 84, it is usually advantageous to place the nonwoven side facing out away from the user. In addition, in such embodiments it may be possible to utilize the nonwoven portion of the laminate as the loop portion of the hook and loop combination.

Other uses for the filled film and breathable film/support layer laminates according to the present invention include, but are not limited to, medical protective articles such as surgical drapes and gowns, as well as wipers, barrier materials and articles of clothing or portions thereof including such items as workwear and lab coats.

The advantages and other characteristics of the present invention are best illustrated by the following examples:

EXAMPLES

Eight resin compositions listed in Table I below were compounded. Films were formed and stretched in a machine-direction orientator in accordance to the condition listed in Table I below.

TABLE I

| | FILM COMPOSITION | FILM TYPE | STRETCH RATIO | STRETCH CONDITION TEMPERATURE (° F.) STRETCH | ANNEAL | FINAL BASIS WEIGHT (g/m$^2$) |
|---|---|---|---|---|---|---|
| A | 55% Supercoat ™ CaCO$_3$ (1 micron average particle size) from English China Clay America Inc. Sylacauga, Alabama 40% Dowlex ® NG3347A (2.3 MI) octene | Blown | 4.25 | 160 | 215 | 15 |

TABLE I-continued

| FILM COMPOSITION | FILM TYPE | STRETCH RATIO | STRETCH CONDITION TEMPERATURE (° F.) STRETCH | ANNEAL | FINAL BASIS WEIGHT (g/m$^2$) |
|---|---|---|---|---|---|
| LLDPE Dow Chemical Corp. Midland, MI 5% Exxon LD-134.09 (2 MI) LDPE Exxon Chemical Co. Houston, TX | | | | | |
| B 55% Supercoat ™ CaCO$_3$ (1 micron average particle size) from English China Clay America Inc. Sylacauga, Alabama 30% LLDPE blend: Dowlex ® 2517 and Dowlex ® 2532 (1:4) 10 MI (melt index) 15% Dowlex ® LLDPE 2045 1 MI (melt index) | Blown | 4.25 | 160 | 215 | 12 |
| C 48% Supercoat ™ CaCO$_3$ (1 micron average particle size) from English China Clay America Inc. Sylacauga, Alabama 47% Dowlex ® NG3347A octene LLDPE (2.3 MI) 5% Dow 640 LDPE (2 MI) | Blown | 4.0 | 160 | 220 | 18 |
| D 48% Supercoat ™ CaCO$_3$ (1 micron average particle size) from English China Clay America Inc. Sylacauga, Alabama 47% Dowlex ® NG3310 octene LLDPE (3.5 MI) 5% Dow 722 LDPE (8 MI) | Cast | 4.0 | 160 | 215 | 16 |
| E 47% Supercoat ™ CaCO$_3$ CaCO$_3$ (1 micron average particle size) from English China Clay America Inc. Sylacauga, Alabama 48% Dow Affinity ™ PL-1845 octene LLDPE (3.5 MI) Metallocene ρ = 0.910 g/cc 5% Dow 5004 LDPE (4 MI) | Cast | 3.25 | 160 | 190 | 18 |
| F 48% Supercoat ™ CaCO$_3$ CaCO$_3$ (1 micron average particle size) from English China Clay America Inc. Sylacauga, Alabama 52% Dow Affinity ™ PL 1280 octene LLDPE (5 MI) ρ = 0.900 g/cc | Cast | 4.25 | 160 | 180 | 15 |
| G 55% Supercoat ™ CaCO$_3$ CaCO$_3$ (1 micron average particle size) from English China Clay America Inc. Sylacauga, Alabama 15% Himont X-11395-5-1 Catalloy ™ Reactor TPO-5MFR (melt flow | Blown | 4.25 | 160 | 215 | 17 |

TABLE I-continued

| FILM COMPOSITION | | FILM TYPE | STRETCH RATIO | STRETCH CONDITION TEMPERATURE (° F.) | | FINAL BASIS WEIGHT (g/m²) |
|---|---|---|---|---|---|---|
| | | | | STRETCH | ANNEAL | |
| | rate) Himont Incorporated, Wilmington, DE 15% LLDPE blend: Dowlex ® 2517 and Dowlex ® 2532 (1:4) 10 MI (melt index) 15% Dowlex ® 2045 1 MI (melt index) | | | | | |
| H | 55% Supercoat ™ CaCO₃ CaCO₃ (1 micron average particle size) from English China Clay America Inc. Sylacauga, Alabama 45% Union Carbide 6D81 (copolymer of propylene and 5.5% ethylene) (5.5 MFR) Union Carbide Corp. Danbury, CT | Blown | 4.25 | 160 | 215 | 14 |

WVTR and cross-machine direction break elongation characteristics of each stretched film were measured in accordance to the procedures listed below. The results of these measurements are listed in Table II below.

Tensile Test

The film peak load ("CD tensile strength") and elongation at peak load (critical break elongation 90° to the direction of orientation in this case, "critical CD break elongation") were determined in accordance with Method 5102 Federal Test Methods Standard Number 191A. Sample sizes were three inch by six inches (2.54 cm×15.24 cm) with the cross machine direction of the sample running parallel to the six inch length of the sample. Three samples were run for each material and the values were averaged. The jaws of the tensile tester were three inches wide, the initial gap or gauge length was three inches (7.62 cm) and the crosshead speed was 12 inches per minute (305 mm/min).

Water Vapor Transmission Data

The water vapor transmission rate (WVTR) for the sample materials was calculated in accordance with ASTM Standard E96-80. Circular samples measuring three inches in diameter were cut from each of the test materials and a control which was a piece of CELGARD® 2500 film from Hoechst Celanese Corporation of Sommerville, N.J. CELGARD® 2500 film is a microporous polypropylene film. Three samples were prepared for each material. The test dish was a No. 60-1 Vapometer pan distributed by Thwing-Albert Instrument Company of Philadelphia, Pa. One hundred milliliters of water were poured into each Vapometer pan and individual samples of the test materials and control material were placed across the open tops of the individual pans. Screw-on flanges were tightened to form a seal along the edges of the pan, leaving the associated test material or control material exposed to the ambient atmosphere over a 6.5 centimeter diameter circle having an exposed area of approximately 33.17 square centimeters. The pans were placed in a forced air oven at 100° F. (37.8° C.) for 1 hour to equilibrate. The oven was a constant temperature oven with external air circulating through it to prevent water vapor accumulation inside. A suitable forced air oven is, for example, a Blue M Power-O-Matic 60 oven distributed by Blue M Electric Company of Blue Island, Ill. Upon completion of the equilibration, the pans were removed from the oven, weighed and immediately returned to the oven. After 24 hours, the pans were removed from the oven and weighed again. The preliminary test water vapor transmission rate values were calculated with Equation (I) below:

$$\text{Test WVTR} = (\text{grams weight loss over 24 hours}) \times 315.5 \text{ g/m}^2/24 \text{ hrs} \qquad (I)$$

The relative humidity within the oven was not specifically controlled.

Under predetermined set conditions of 100° F. (37.8° C.) and ambient relative humidity, the WVTR for the CELGARD® 2500 control has been defined to be 5000 grams per square meter for 24 hours. Accordingly, the control sample was run with each test and the preliminary test values were corrected to set conditions using equation II below:

$$\text{WVTR} = (\text{Test WVTR/control WVTR}) \times (5000 \text{ g/m}^2/24 \text{ hrs.}) \qquad (II)$$

TABLE II

| FILM | WVTR (g/m²-24 hours) | CROSS-MACHINE DIRECTION BREAK ELONGATION (%) | CD TENSILE STRENGTH g/3" WIDTH |
|---|---|---|---|
| A | 4212 | 261 | 423 |
| B | 4442 | 21 | 435 |
| C | 1742 | 422 | 682 |
| D | 2076 | 345 | 605 |
| E | 2726 | 433 | 617 |
| F | 2403 | 524 | 515 |
| G | 2808 | 390 | 507 |
| H | 3338 | 249 | 744 |

As shown in Table II above, a film of the present invention (films A) has superior cross-machine direction break elongation (a measure of toughness) when compared to film B, which contains the same amount of filler and has similar WVTR value as film A. In addition, although films G and H have increased toughness at the same filler content, their WVTR value values were inferior to that of the film of the present invention (film A). The data relating to films C, D, E, F listed in Table II above show that these films of the present invention may have good controllable WVTR and excellent toughness with lower filler content.

Example 2

Films A, G and H listed in Table I above were each used for preparing laminations. A sheet of absorbent material comprising polypropylene meltblown fibers mixed with pulp fibers, also known as coform, was directed under a spray-head where it was sprayed with a hotmelt adhesive, such as NS-5610 available from National Starch & Chemical Co. of Bridgewater, N.J., at 350° F. temperature at a rate of about 2 grams per square meter. One of the above films was unwound from a roll and lead to a pair of niprolls where the film and the sprayed absorbent were contacted to form a laminate which was then wound into a roll. Subsequently a layer of spunbond of 0.8 ounce per square yard basis weight was attached to the film side of the laminate by the identical hotmelt laminating process. The WVTR of the three-layer laminates with each of the films was measured and compared to that of the films. The WVTR of the laminate with film A decreased to 4220 g/m²-24 hrs from the film's 4735, a 10.9% drop. The drop with laminate of the G film was 33.4% (to 2143 from 3220), and the drop with laminate of the H film was 28% (to 2278 from 3163). As evident from the above example, the WVTR's of the films containing Catalloy™ (G) or a copolymer of polypropylene (H), already starting from lower values, declined substantially more than the WVTR with film A, the subject of the present invention.

This illustrates the stability of film of the present invention. Films C, D, E and F, not containing the undesirable unstable components were not found to be unstable or otherwise thermally sensitive to declines in breathability.

Therefore, the films of the present invention have high water vapor transmission rate and toughness that impart a wide variety of functionalities including vapor permeability, liquid impermeability, and comfort. Furthermore, such films can be attached to support layers to form laminates.

Of course, it should be understood that a wide range of changes and modifications can be made to the embodiments described above. It is therefore intended that the foregoing description illustrates rather than limits this invention, and that it is the following claims, including all equivalents, which define this invention.

We claim:

1. A stretch-oriented thermoplastic film comprising:
    a filled resin including at least one copolymer of ethylene with at least one $C_4$–$C_8$ α-olefin monomer wherein said resin comprises super-octene resins or metallocene-catalyzed ethylene-based copolymers and from about 40 to about 65% by weight of said filled resin material further comprising calcium carbonate and filler that contributes to pore formation;
    wherein said film has a water vapor transmission rate of from about 300 to about 4,500 g/m²-24 hours;
    wherein said film has a critical break elongation 90° to the direction of orientation of greater than about 100%.

2. The film of claim 1 wherein said critical break elongation 90° to the direction of orientation is greater than about 150%.

3. The film of claim 1 wherein said water vapor transmission rate remained essentially constant after exposing said film to elevated temperatures.

4. The film of claim 1 wherein said calcium carbonate includes a plurality of particles having a fatty acid coating.

5. The film of claim 1 wherein:
    said calcium carbonate is present in an amount of about 48% by weight of said resin material; and
    said water vapor transmission rate is about 1,500 g/m²/24 hours.

6. The film of claim 1 wherein said film is uniaxially oriented.

7. A personal care absorbent article comprising a liquid permeable top sheet and a back sheet with an absorbent core disposed therebetween, at least one of said back sheet and said top sheet including the film of claim 1.

8. The article of claim 7 wherein said article is a diaper.

9. The article of claim 7 wherein said article is a training pant.

10. The article of claim 7 wherein said article is selected from a sanitary napkin or menstrual panty.

11. The article of claim 7 wherein said article is a incontinence device.

12. A process for making a microporous film comprising the steps of:
    providing a resin including a nonelastic material comprising at least one copolymer of ethylene with at least one $C_4$–$C_8$ α-olefin monomer wherein said material is further selected from the group comprising super-octene resins or metallocene-catalyzed ethylene-based copolymers;
    adding to said resin material from about 40 to about 65% by weight of said filled resin material of calcium carbonate that contributes to pore formation to form a filled resin;
    extruding said filled resin to form a film;
    stretching said film to form a microporous film;
    wherein said film has a critical break elongation 90° to the direction of orientation of greater than about 100%.

13. The process of claim 12 wherein said nonelastic material is provided in an amount of at least about 30% by weight of said filled resin.

14. The process of claim 12 wherein said film is uniaxially stretched.

15. The process of claim 12 wherein:
    said calcium carbonate is present in an amount of about 48% by weight of said filled resin; and
    said water vapor transmission rate is about 1,500 g/m²/24 hours.

16. The process of claim 12 wherein said water vapor transmission rate of said microporous film remained essentially constant after exposing said film to elevated temperatures.

17. A microporous film prepared by the process of claim 12.

18. A uniaxially oriented thermoplastic film comprising:
    a filled resin including a nonelastic material comprising at least one copolymer of ethylene with at least one $C_4$–$C_8$ α-olefin monomer wherein said material comprises super-octene resins or metallocene-catalyzed ethylene-based copolymers, said filled resin further comprising from about 40 to about 65% by weight of said filled resin material of calcium carbonate having a particle size of from about 0.5 to about 8 microns;
    wherein said film has a water vapor transmission rate of from about 300 to about 4,500 g/m²-24 hours;

wherein said film has a critical break elongation 90° to the direction of orientation of greater than about 100%.

19. The film of claim 18 wherein said filled resin includes at least 30 weight percent of said nonelastic material.

20. The film of claim 18 wherein said nonelastic material is a metallocene-catalyzed ethylene-based with a density of at least about 0.900 g/cc.

21. A breathable laminate comprising:

a thermoplastic film including a filled resin including at least one copolymer of ethylene with at least one $C_4$–$C_8$ α-olefin monomer wherein said resin comprises super-octene resins or metallocene-catalyzed ethylene-based copolymers and from about 40 to about 65% by weight of said filled resin material of calcium carbonate that contributes to pore formation; and at least one support layer bonded to said film layer wherein said film has a critical break elongation 90° to the direction of orientation is greater than about 100%.

22. The laminate of claim 21 wherein said critical break elongation 90° to the direction of orientation is greater than about 150%.

23. The laminate of claim 21 wherein said calcium carbonate is present in an amount of about 48% by weight of said resin material; and said film has a water vapor transmission rate of about 1,500 g/m$^2$/24 hours.

24. The laminate of claim 21 wherein said support layer is a fibrous nonwoven web.

25. A personal care absorbent article comprising a liquid permeable top sheet and a back sheet with an absorbent core disposed therebetween, at least one of said back sheet and said top sheet including the laminate of claim 21.

26. The article of claim 25 wherein said article is a diaper.

27. The article of claim 25 wherein said article is a training pant.

28. The article of claim 25 wherein said article is selected from a sanitary napkin and a menstrual panty.

29. The article of claim 25 wherein said article is a incontinence device.

30. The article of claim 25 wherein said article is a bandage.

31. A process for forming a breathable laminate comprising:

providing a filled film layer comprising from about 40 to about 65% by weight of calcium carbonate having a particle size that contributes to pore formation and a linear low density polyethylene polymeric material including at least one copolymer of ethylene with at least one $C_4$–$C_8$ α-olefin monomer wherein said material comprises super-octene resins or metallocene-catalyzed ethylene-based copolymers;

stretching said filled film to produce a microporous film;

bonding at least one support layer to said microporous film to form a laminate.

32. The process of claim 31 wherein said support layer is thermally bonded to said microporous film.

33. The process of claim 31 wherein said support layer is bonded to said microporous film with a hot melt adhesive.

34. The process of claim 31 wherein said filled film is uniaxially stretched.

35. A medical garment comprising:

a thermoplastic film including a filled resin including at least one copolymer of ethylene with at least one $C_4$–$C_8$ α-olefin monomer wherein said resin comprises super-octene resins or metallocene-catalyzed ethylene-based copolymers and from about 40 to about 65% by weight of said filled resin material of calcium carbonate that contributes to pore formation; and at least one support layer bonded to said film layer wherein said film has a critical break elongation 90° to the direction of orientation of greater than about 100%.

36. The film of claim 35 wherein said critical break elongation 90° to the direction of orientation of greater than about 150%.

* * * * *

UNITED STATES PATENT AND TRADEMARK OFFICE
CERTIFICATE OF CORRECTION

PATENT NO. : 6,096,014  
DATED : August 1, 2000  
INVENTOR(S) : William B. Haffner et al.

Page 1 of 1

It is certified that error appears in the above-identified patent and that said Letters Patent is hereby corrected as shown below:

Column 16, claim 12,
Lines 26-31, first paragraph, should read -- providing a resin including a nonelastic material comprising at least one copolymer of ethylene with at least one $C_4$-$C_8$ α-olefin monomer wherein said material comprises super-octene resins or metallocene-catalyzed ethylene-based copolymers; --

Signed and Sealed this

Eighteenth Day of December, 2001

Attest:

Attesting Officer

JAMES E. ROGAN
Director of the United States Patent and Trademark Office

UNITED STATES PATENT AND TRADEMARK OFFICE
CERTIFICATE OF CORRECTION

PATENT NO.   : 6,096,014
DATED        : August 1, 2000
INVENTOR(S)  : William B. Haffner et al.

It is certified that error appears in the above-identified patent and that said Letters Patent is hereby corrected as shown below:

Column 15, claim 1,
Lines 54-60, first paragraph, should read
-- a filled resin including at least one copolymer of ethylene with at least one $C_4$-$C_8$ α-olefin monomer wherein said resin comprises super-octene resins or metallocene-catalyzed ethylene-based copolymers and from about 40 to about 65% by weight of said filled resin material further comprising calcium carbonate filler that contributes to pore formation; --

Signed and Sealed this

Ninth Day of April, 2002

*Attest:*

*Attesting Officer*

JAMES E. ROGAN
*Director of the United States Patent and Trademark Office*